United States Patent
Kumar

[11] Patent Number: 6,022,497
[45] Date of Patent: Feb. 8, 2000

[54] PHOTOCHROMIC SIX-MEMBERED HETEROCYCLIC-FUSED NAPHTHOPYRANS

[75] Inventor: Anil Kumar, Pittsburgh, Pa.

[73] Assignee: PPG Industries Ohio, Inc., Cleveland, Ohio

[21] Appl. No.: 09/273,086

[22] Filed: Mar. 19, 1999

Related U.S. Application Data

[63] Continuation-in-part of application No. 09/114,102, Jul. 10, 1998, abandoned.

[51] Int. Cl.⁷ ............ G02B 5/23; C07D 265/12; C07D 239/00; C07D 319/00; C07D 311/78
[52] U.S. Cl. ............ 252/586; 544/89; 544/247; 544/150; 544/375; 549/274; 549/277; 549/278; 549/58; 549/60; 546/282.4; 546/283.1; 548/454; 548/525; 548/196
[58] Field of Search ............ 252/586; 544/89, 544/247, 150, 375; 549/274, 277, 278, 58, 60; 548/454, 525, 196; 546/282.4, 283.1

[56] References Cited

U.S. PATENT DOCUMENTS

| | | | |
|---|---|---|---|
| 3,567,605 | 3/1971 | Becker | 204/158 |
| 3,627,690 | 12/1971 | Casella et al. | 252/300 |
| 4,818,096 | 4/1989 | Heller et al. | 351/163 |
| 5,066,818 | 11/1991 | Van Gemert et al. | 549/389 |
| 5,429,774 | 7/1995 | Kumar | 549/383 |
| 5,458,814 | 10/1995 | Kumar et al. | 252/586 |
| 5,552,091 | 9/1996 | Kumar | 252/586 |
| 5,565,147 | 10/1996 | Knowles et al. | 252/586 |
| 5,645,767 | 7/1997 | Van Gemert | 252/586 |
| 5,674,432 | 10/1997 | Knowles et al. | 252/586 |
| 5,783,116 | 7/1998 | Lin | 252/586 |
| 5,840,926 | 11/1998 | Hughes | 252/586 |
| 5,869,662 | 2/1999 | Hughes | 252/586 |

*Primary Examiner*—Philip Tucker
*Attorney, Agent, or Firm*—Frank P. Mallak; Irwin M. Stein

[57] ABSTRACT

Described are novel photochromic six-membered heterocyclic-fused naphthopyran compounds, examples of which are naphthopyran compounds having a substituted or unsubstituted six-membered heterocyclic group fused to one side of the naphtho portion of the naphthopyran and having certain substituents at the position ortho to the oxygen atom of the naphthopyran ring. These compounds may be represented by the following graphic formula:

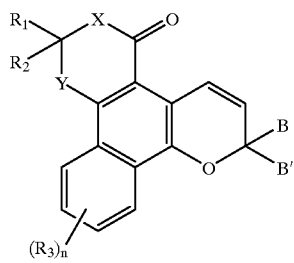

Also described are polymeric organic host materials that contain or that are coated with such compounds or combinations thereof with complementary photochromic compounds, e.g., certain other naphthopyrans, benzopyrans, and spiro(indoline) type compounds.

22 Claims, No Drawings

PHOTOCHROMIC SIX-MEMBERED HETEROCYCLIC-FUSED NAPHTHOPYRANS

CROSS REFERENCE TO RELATED APPLICATIONS

This application is a continuation-in-part of U.S. Ser. No. 09/114,102, filed Jul. 10, 1998 now abandoned.

DESCRIPTION OF THE INVENTION

The present invention relates to certain novel naphthopyran compounds. More particularly, this invention relates to novel photochromic naphthopyran compounds having a six-membered heterocyclic ring fused to the naphtho portion of the molecule and to compositions and articles containing such novel naphthopyran compounds. When exposed to electromagnetic radiation containing ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −30° C. Irradiation of the compounds with visible light or upon raising the temperature to above about 0° C. is reported to reverse the coloration to a colorless state.

U.S. Pat. No. 5,066,818 describes various 3,3-diaryl-3H-naphtho[2,1-b]pyrans as having desirable photochromic properties, i.e., high colorability and acceptable fade, for ophthalmic and other applications. Also disclosed by way of comparative example in the '818 patent are the isomeric 2,2-diaryl-2H-naphtho[1,2-b]pyrans, which are reported to require unacceptably long periods of time to fade after activation.

U.S. Pat. No. 3,627,690 describes photochromic 2,2-di-substituted-2H-naphtho[1,2-b]pyran compositions containing minor amounts of either a base or weak-to-moderate strength acid. The addition of either an acid or base to the naphthopyran composition is reported to increase the fade rate of the colored naphthopyrans, thereby making them useful in eye protection applications such as sunglasses. It is reported therein further that the fade rate of 2H-naphtho[1,2-b]pyrans without the aforementioned additives ranges from several hours to many days to reach complete reversion.

U.S. Pat. No. 4,818,096 discloses purple/blue coloring photochromic benzo- or naphthopyrans having at the position alpha to the oxygen of the pyran ring a phenyl group having a nitrogen containing substituent in the ortho or para positions. U.S. Pat. No. 5,645,767 describes novel photochromic indeno-fused 2H-naphtho[1,2-b]pyran compounds, the 2,1-positions of the indeno group being fused to the f side of the naphthopyran.

U.S. Pat. No. 5,458,814 discloses photochromic 2H-naphtho[1,2-b]pyran compounds having certain substituents at the number 5 and 6 carbon atoms of the naphtho portion of the naphthopyran and at the 2-position of the pyran ring. These compounds have an acceptable fade rate in addition to a high activated intensity and a high coloration rate.

The present invention relates to novel substituted naphtho[1,2-b]pyran compounds having a substituted or unsubstituted six-membered heterocyclic group fused to the f side of the naphtho portion of the naphthopyran with certain substituents at the position ortho to the oxygen atom of the naphthopyran, which compounds may be represented by graphic formula I. These compounds have demonstrated an acceptable fade rate without the addition of acids or bases, a high activated intensity and a high coloration rate.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-à-vis, glass lenses. Moreover, photochromic transparencies for vehicles, such as cars and airplanes, have been of interest because of the potential safety features that such transparencies offer.

In accordance with the present invention, it has now been discovered that certain novel dioxino, oxazino, pyrimidino and pyrano-fused naphtho[1,2-b]pyrans having activated colors ranging from red to violet, an acceptable fade rate, high activated intensity and a high coloration rate may be prepared. These compounds may be described as naphtho[1,2-b]pyrans having a six-membered heterocyclic ring fused to the f side of the basic naphthopyran structure and having certain substituents at the position ortho to the oxygen atom of the basic naphthopyran. In particular, the compounds include dioxino[5',4':3,4]naphtho[1,2-b]pyrans, oxazino[5',4':3,4]naphtho[1,2-b]pyrans, oxazino[5',6':3,4]naphtho[1,2-b]pyrans, pyrano[3',4':3,4]naphtho[1,2-b]pyrans and pyrimidino[5',4':3,4]naphtho[1,2-b]pyrans, each having an oxo group substituted at the number 4 position and certain substituents at the number 2 position with certain other substituents optionally present at the number 9, 10, 11 or 12 positions.

These aforedescribed compounds may be represented by the following graphic formula I in which the letters a through n represent the sides of the naphthopyran, and the numbers 1 through 12 inside the rings identify the numbering sequence of the ring atoms of the six-membered heterocyclic-fused naphthopyran.

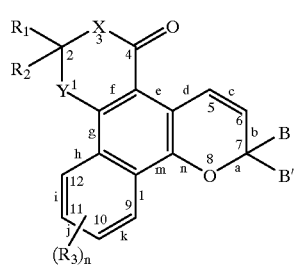

I

In graphic formula I, $R_1$ and $R_2$ may together form an oxo group. Alternatively, $R_1$ is hydrogen and $R_2$ may be hydrogen, $C_1$–$C_6$ alkyl, $C_3$–$C_7$ cycloalkyl, allyl, phenyl, mono- and di-substituted phenyl, benzyl, mono-substituted benzyl, naphthyl, mono- and di-substituted naphthyl, $C_4$–$C_{12}$ bicycloalkyl, linear or branched $C_3$–$C_{12}$ alkenyl, $C_1$–$C_6$ alkoxycarbonyl($C_1$–$C_6$)alkyl, methacryloxy($C_1$–$C_6$) alkyl, acryloxy($C_1$–$C_6$)alkyl, $C_1$–$C_4$ acyloxy($C_1$–$C_6$)alkyl or $C_1$–$C_6$ alkoxy($C_1$–$C_6$)alkyl or the unsubstituted, mono- or di-substituted heteroaromatic groups pyridyl, furanyl, benzofuran-2-yl, benzyfuran-3-yl, thienyl, benzothien-2-yl, benzothien-3-yl, dibenzofuranyl, dibenzothienyl, carbazolyl, benzopyridyl and indolyl. Each of the phenyl, benzyl, naphthyl and heteroaromatic group substituents may be $C_1$–$C_6$ alkyl, $C_1$–$C_6$ alkoxy, morpholino, di($C_1$–$C_6$) alkylamino, chloro or fluoro. Preferably, $R_2$ is selected from the group consisting of hydrogen, $C_1$–$C_5$ alkyl, $C_3$–$C_6$ cycloalkyl, phenyl, mono- or di-substituted phenyl, benzyl and mono-substituted benzyl. Each of the preferred phenyl and benzyl group substituents are $C_1$–$C_4$ alkyl or $C_1$–$C_4$ alkoxy. More preferably, $R_2$ is selected from the group consisting of hydrogen, $C_1$–$C_5$ alkyl and phenyl.

Each $R_3$ in graphic formula I is selected from the group consisting of $C_1$–$C_6$ alkyl, $C_1$–$C_6$ alkoxy, chloro, fluoro, phenyl, mono- and di-substituted phenyl, benzyl or mono-substituted benzyl, $C_3$–$C_7$ cycloalkyl, aryloxy, di($C_1$–$C_6$) alkylamino, morpholino, thiomorpholino, piperidino, pyridyl, tetrahydroquinolino, isoquinolino, aziridino, diarylamino, N—($C_1$–$C_6$)alkyl piperizino and N-aryl piperizino, wherein the aryl groups are phenyl or naphthyl and n is the integer 0, 1 or 2. The phenyl and benzyl substituents are $C_1$–$C_6$ alkyl, $C_1$–$C_6$ alkoxy, fluoro or chloro. Preferably, each $R_3$ is selected from the group consisting of $C_1$–$C_4$ alkyl, $C_1$–$C_4$ alkoxy, fluoro, phenyl and aryloxy, and n is the integer 0, 1, or 2. More preferably, each $R_3$ is selected from the group consisting of $C_1$–$C_3$ alkyl, $C_1$–$C_3$ alkoxy, phenyl and aryloxy and n is the integer 0, 1 or 2.

X in graphic formula I may be oxygen or —N($R_4$)—, wherein $R_4$ is hydrogen, $C_1$–$C_6$ alkyl, $C_3$–$C_7$ cycloalkyl, allyl, vinyl, $C_1$–$C_5$ acyl, phenyl, mono- and di-substituted phenyl, benzyl, mono-substituted benzyl, $C_1$–$C_4$ alkoxycarbonyl($C_1$–$C_6$)alkyl, methacryloxy($C_1$–$C_6$)alkyl, acryloyloxy($C_1$–$C_6$)alkyl, phenyl($C_1$–$C_6$)alkyl, naphthyl, $C_4$–$C_{12}$ bicycloalkyl or $C_2$–$C_4$ acyloxy or the unsubstituted or substituted heteroaromatic groups pyridyl, furanyl, benzofuran-2-yl, benzofuran-3-yl, thienyl, benzothien-2-yl, benzothien-3-yl, dibenzofuranyl, dibenzothienyl, carbazolyl, benzopyridyl and indolyl. Each of the phenyl, benzyl and heteroaromatic group substituents may be $C_1$–$C_6$ alkyl or $C_1$–$C_6$ alkoxy. Preferably, X is oxygen or —$NR_4$—, wherein $R_4$ is hydrogen, $C_1$–$C_3$ alkyl, methacryloxy($C_1$–$C_6$) alkyl or acryloxy($C_1$–$C_6$)alkyl.

Y in graphic formula I may be oxygen, —N($R_4$)— or —C(($R_5$)$R_6$)—, with the proviso that when Y is C(($R_5$) $R_6$)—, X is oxygen. $R_4$ is the same as described for X, $R_5$ and $R_6$ may each be hydrogen, $C_1$–$C_6$ alkyl or $C_3$–$C_7$ cycloalkyl. Preferably, Y is oxygen, —NH— or —$CH_2$—.

B and B' in graphic formula I may each be selected from the group consisting of:
(i) the unsubstituted, mono-, di- and tri-substituted aryl groups, phenyl and naphthyl;
(ii) the unsubstituted, mono- and di-substituted heteroaromatic groups pyridyl, furanyl, benzofuran-2-yl, benzofuran-3-yl, thienyl, benzothien-2-yl, benzothien-3-yl, dibenzofuranyl, dibenzothienyl, carbazolyl benzopyridyl, indolyl and fluorenyl, each of said aryl and heteroaromatic substituents in parts (i) and (ii) being selected from the group consisting of hydroxy, aryl, i.e., phenyl and naphthyl, mono($C_1$–$C_6$) alkoxyaryl, di($C_1$–$C_6$)alkoxyaryl, mono($C_1$–$C_6$) alkylaryl, di($C_1$–$C_6$)alkylaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy($C_1$–$C_6$)alkoxy, aryl($C_1$–$C_6$)alkyl, aryl($C_1$–$C_6$)alkoxy, aryloxy, aryloxy($C_1$–$C_6$)alkyl, aryloxy($C_1$–$C_6$)alkoxy, mono- and di-($C_1$–$C_6$)alkylaryl ($C_1$–$C_6$)alkyl, mono- and di-($C_1$–$C_6$)alkoxyaryl($C_1C_6$) alkyl, mono- and di-($C_1$–$C_6$)alkylaryl($C_1$–$C_6$)alkoxy, mono- and di-($C_1$–$C_6$)alkoxyaryl($C_1$–$C_6$)alkoxy, amino, mono($C_1$–$C_6$)alkylamino, di-($C_1$–$C_6$) alkylamino, diarylamino, piperazino, N—($C_1$–$C_6$) alkylpiperazino, N-arylpiperazino, aziridino, indolino, piperidino, morpholino, thiomorpholino, tetrahydroquinolino, tetrahydroisoquinolino, pyrryl, $C_1$–$C_6$ alkyl, $C_1$–$C_6$ chloroalkyl, $C_1$–$C_6$ fluoroalkyl, $C_1$–$C_6$ alkoxy, mono($C_1$–$C_6$)alkoxy($C_1$–$C_4$)alkyl, acryloxy, methacryloxy, bromo, chloro and fluoro;
(iii) the groups represented by the following graphic formulae:

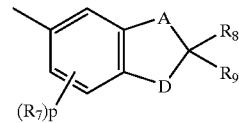

IIA

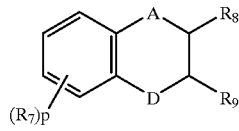

IIB wherein A may be carbon or oxygen and D may be oxygen or substituted nitrogen, provided that when D is substituted nitrogen, A is carbon, said nitrogen substituents being selected from the group consisting of hydrogen, $C_1$–$C_6$ alkyl and $C_2$–$C_6$ acyl; each $R_7$ is $C_1$–$C_6$ alkyl, $C_1$–$C_6$ alkoxy, hydroxy, chloro or fluoro; $R_8$ and $R_9$ are each hydrogen or $C_1$–$C_6$ alkyl; and p is the integer 0, 1 or 2;

(iv) $C_1$–$C_6$ alkyl, $C_1$–$C_6$ chloroalkyl, $C_1$–$C_6$ fluoroalkyl, $C_1$–$C_6$ alkoxy($C_1$–$C_4$)alkyl, $C_3$–$C_6$ cycloalkyl, mono ($C_1$–$C_6$)alkoxy($C_3$–$C_6$)cycloalkyl, mono($C_1$–$C_6$)alkyl ($C_3$–$C_6$)cycloalkyl, chloro($C_3$–$C_6$)cycloalkyl, fluoro ($C_3$–$C_6$)cycloalkyl and $C_4$–$C_{12}$ bicycloalkyl; and (v) the group represented by the following graphic formula:

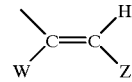

IIC wherein W in graphic formula IIC may be hydrogen or $C_1$–$C_4$ alkyl and Z in graphic formula IIC may be selected from the unsubstituted, mono-, and di-substituted members of the group consisting of naphthyl, phenyl, furanyl and thienyl, each of said group substituents in this part (v) being $C_1$–$C_4$ alkyl, $C_1$–$C_4$ alkoxy, fluoro or chloro; or (vi) B and B' taken together form fluoren-9-ylidene, mono-, or di-substituted fluoren-9-ylidene or form a member selected from the group consisting of saturated $C_3$–$C_{12}$ spiro-monocyclic hydrocarbon rings, e.g., cyclopropylidene, cyclobutylidene, cyclopentylidene, cyclohexylidene, cycloheptylidene, cyclooctylidene, cyclononylidene, cyclodecylidene, cycloundecylidene, cyclododecylidene; saturated $C_7$–$C_{12}$ spirobicylic hydrocarbon rings, e.g., bicyclo[2.2.1]heptylidene, i.e., norbornylidene, 1,7,7-trimethyl bicyclo[2.2.1] heptylidene, i.e., bornylidene, bicyclo[3.2.1] octylidene, bicyclo[3.3.1]nonan-9-ylidene, bicyclo

[4.3.2]undecane, and saturated $C_7$–$C_{12}$ spiro-tricyclic hydrocarbon rings, e.g., tricyclo[2.2.1.0$^{2,6}$]heptylidene, tricyclo[3.3.1.1$^{3,7}$]decylidene, i.e., adamantylidene, and tricyclo[5.3.1.1$^{2,6}$]dodecylidene, each of said fluoren-9-ylidene substituents being selected from the group consisting of $C_1$–$C_4$ alkyl, $C_1$–$C_4$ alkoxy, fluoro and chloro.

More preferably, B and B' are each selected from the group consisting of:

(i) phenyl, mono-substituted phenyl and di-substituted phenyl;

(ii) the unsubstituted, mono- and di-substituted heteroaromatic groups furanyl, benzofuran-2-yl, thienyl, benzothien-2-yl, dibenzofuranyl, aryloxy and diarylamino, each of said phenyl and heteroaromatic substituents in parts (i) and (ii) being selected from the group consisting of di($C_1$–$C_3$)alkylamino, piperidino, morpholino, pyrryl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$)alkoxy ($C_1$–$C_3$)alkyl, fluoro and chloro;

(iii) the groups represented by the graphic formulae IIA and IIB, wherein A is carbon and D is oxygen, $R_7$ is $C_1$–$C_3$ alkyl or $C_1$–$C_3$ alkoxy, $R_8$ and $R_9$ are each hydrogen or $C_1$–$C_4$ alkyl, and p is the integer 0 or 1;

(iv) $C_1$–$C_4$ alkyl; and (v) the group represented by the graphic formula IIC wherein W is hydrogen or methyl and Z is phenyl or mono-substituted phenyl, said phenyl substituent being selected from the group consisting of $C_1$–$C_3$ alkyl, $C_1$–$C_3$ alkoxy and fluoro; or (vi) B and B' taken together form fluoren-9-ylidene, mono-substituted fluoren-9-ylidene or a member selected from the group consisting of saturated $C_3$–$C_8$ spiro-monocyclic hydrocarbon rings, saturated $C_7$–$C_{10}$ spiro-bicyclic hydrocarbon rings, and saturated $C_7$–$C_{10}$ spiro-tricyclic hydrocarbon rings, said fluoren-9-ylidene substituent being selected from the group consisting of $C_1$–$C_3$ alkyl, $C_1$–$C_3$ alkoxy, fluoro and chloro.

Most preferably, B and B' are each selected from the group consisting of:

(i) phenyl, mono- and di-substituted phenyl;

(ii) the unsubstituted, mono- and di-substituted heteroaromatic groups furanyl, benzofuran-2-yl, thienyl, benzothien-2-yl, dibenzofuranyl, aryloxy and diarylamino, each of said phenyl and heteroaromatic substituents in parts (i) and (ii) being selected from the group consisting of $C_1$–$C_3$ alkyl, $C_1$–$C_3$ alkoxy and fluoro; and (iii) the group represented by graphic formula IIA, wherein A is carbon and ID is oxygen, $R_7$ is $C_1$–$C_3$ alkyl or $C_1$–$C_3$ alkoxy, $R_8$ and $R_9$ are each hydrogen or $C_1$–$C_3$ alkyl, and p is the integer 0 or 1; or (iv) B and B' taken together form fluoren-9-ylidene, adamantylidene, bornylidene, norbornylidene, or bicyclo[3.3.1]nonan-9-ylidene.

The compounds represented by graphic formula I wherein X and Y are each oxygen and are prepared according to Reactions A–D. Benzophenones represented by graphic formula V and VA are either purchased or prepared by Friedel-Crafts methods using an appropriately substituted or unsubstituted benzoyl chloride of graphic formula IV and a commercially available substituted or unsubstituted benzene compound of graphic formula III. See the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992.

The compounds represented by graphic formulae III and IV are dissolved in a solvent, such as carbon disulfide or methylene chloride, and reacted in the presence of a Lewis acid, such as aluminum chloride or tin tetrachloride, to form the corresponding substituted benzophenone represented by graphic formula V (or VA in Reaction B). R and R' represent potential phenyl substituents, as described hereinbefore.

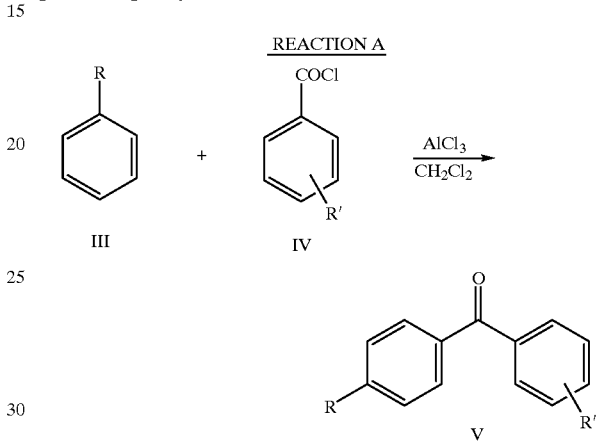

In Reaction B, the substituted or unsubstituted ketone represented by graphic formula VA, in which B and B' may represent groups other than substituted or unsubstituted phenyl, is reacted with sodium acetylide in a suitable solvent, such as anhydrous tetrahydrofuran (THF), to form the corresponding propargyl alcohol represented by graphic formula VI. Propargyl alcohols having B or B' groups other than substituted and unsubstituted phenyl may be prepared from commercially available ketones or for example, from ketones prepared via reaction of an acyl halide with a substituted or unsubstituted benzene, naphthalene, or heteroaromatic compound. Propargyl alcohols having B or B' groups represented by graphic formula IIC may be prepared by the methods described in U.S. Pat. No. 5,274,132, column 2, lines 40 to 68.

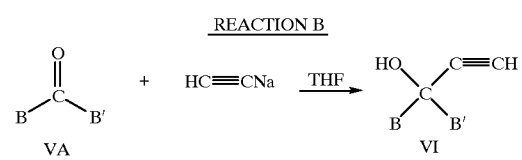

In Reaction C, the naphthol represented by graphic formula VII is prepared by the methods disclosed in U.S. Pat. No. 5,162,570, incorporated herein by reference, and coupled with the propargyl alcohol represented by graphic formula VI in the presence of a catalytic amount of an acid, e.g., p-toluene sulfonic acid in a suitable solvent, such as toluene or chloroform, to produce the 5-phenoxycarbonyl-6-hydroxy naphtho[1,2-b]pyran represented by graphic formula VIII.

REACTION C

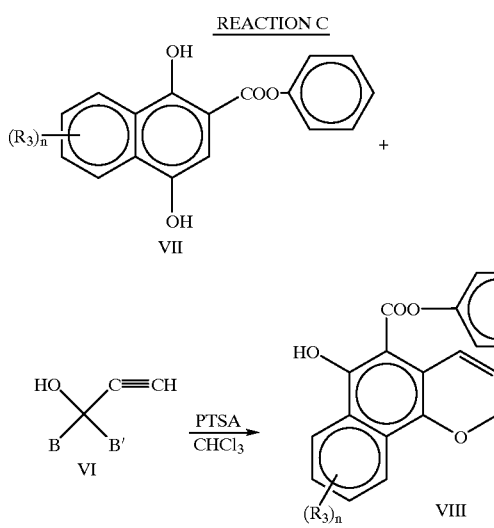

In Reaction D, the naphthopyran represented by graphic formula VIII is reacted with a commercially available aldehyde (R"CHO) in the presence of a slight excess of an amine, e.g., triethylamine (NEt₃) or DABCO, i.e., 1,4-diazabicyclo(2.2.2)octane or triethylenediamine, in a suitable solvent such as chloroform, to form compounds represented by graphic formula IX. R" represents the individual substituents that $R_2$ may be and $R_1$ is hydrogen.

REACTION D

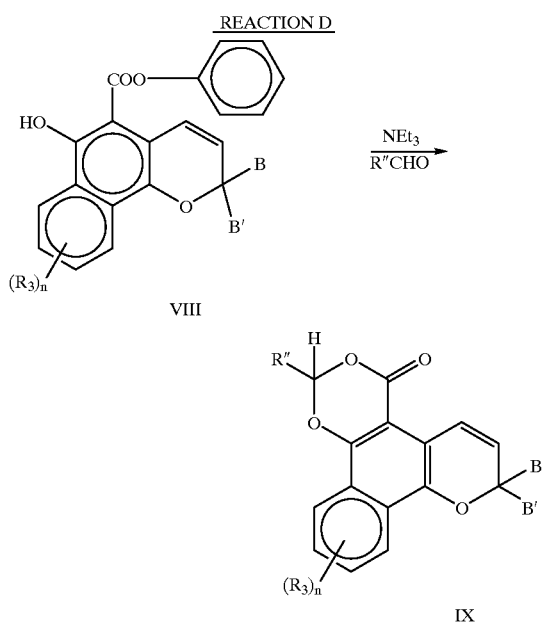

The compounds represented by graphic formula I wherein X is —N($R_4$)— and Y is oxygen are prepared according to Reaction E as follows. The naphthopyran represented by graphic formula X, prepared according to the methods disclosed in U.S. Pat. No. 5,458,814 (hereinafter the '814 patent), is reacted with an isocyanate ($R_4$NCO) in the presence of triethylamine and a catalytic amount of 4-dimethylaminopyridine (DMAP) in a suitable solvent, such as dimethyl formamide (DMF) to form the [1,3]oxazino[5',6':3,4]naphtho[1,2-b]pyran represented by graphic formula XI.

REACTION E

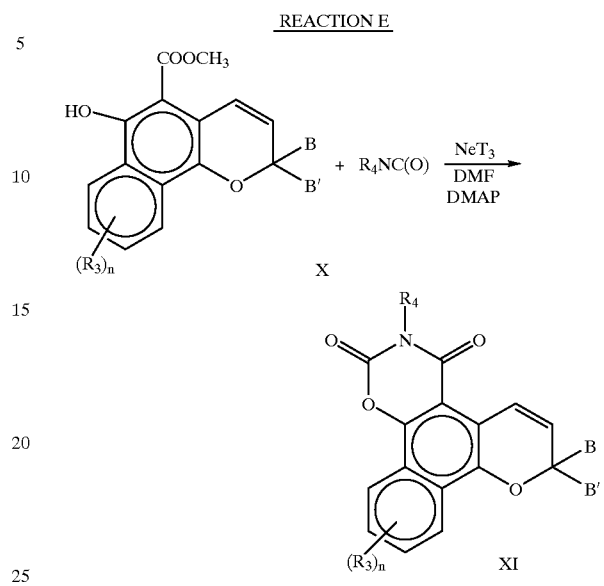

Alternatively, the compounds represented by graphic formula I wherein X is oxygen or —N($R_4$)— and Y is —N($R_4$)—, e.g., where $R_4$ is hydrogen, may be prepared according to Reaction F. The procedure of Reaction F may also be used to prepare compounds of graphic formula I when $R_4$ is a substituent other than hydrogen. The naphthopyran represented by graphic formula XA, which may be prepared according to the '814 patent, is reacted with the substituted imino Grignard reagent represented by graphic formula XII in a suitable solvent, such as THF, to produce the corresponding pyrimido-fused naphthopyran represented by graphic formula XIII as the major product and the oxazino-fused naphthopyran represented by graphic formula XIV as the minor product.

REACTION F

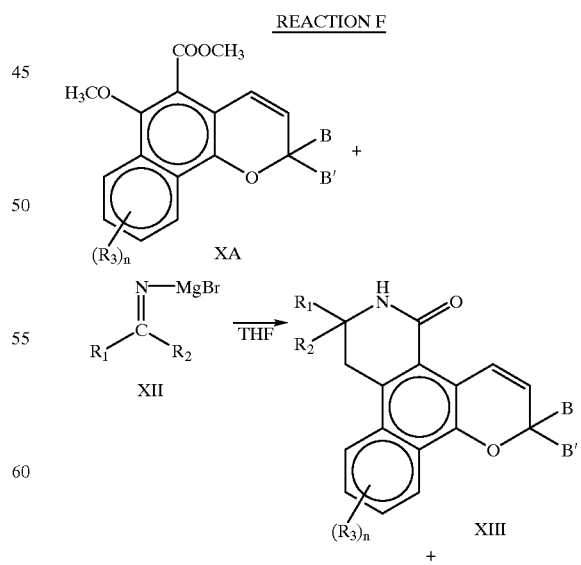

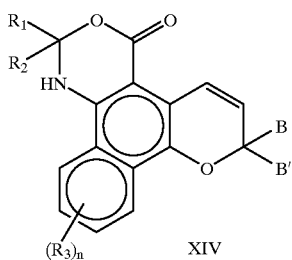

XIV

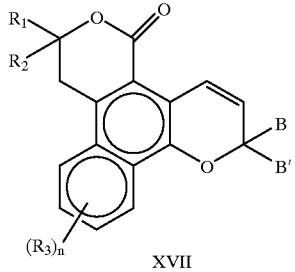

XVII

The compounds represented by graphic formula I wherein X is oxygen and Y is —C((R₅)R₆)—, e.g., —CH₂—, are prepared according to Reactions G and H. In Reaction G, the naphthopyran represented by graphic formula XA is reacted with the vinylic Grignard reagent represented by graphic formula XV in a suitable solvent, such as THF, yielding the corresponding substituted naphthopyran represented by graphic formula XVI.

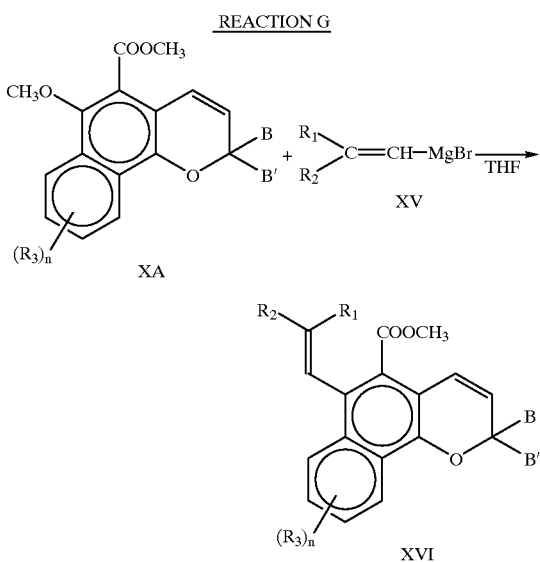

REACTION G

In Reaction H, compound XVI is cyclized by reaction with trimethyl silyl chloride in the presence of sodium iodide in a suitable solvent, such as acetonitrile (ACN), to form compounds represented by graphic formula XVII.

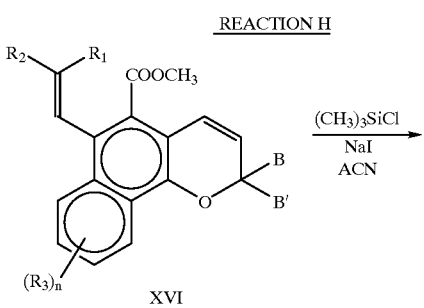

REACTION H

Compounds represented by graphic formula I may be used in those applications in which organic photochromic substances may be employed, e.g., optical lenses, e.g., vision correcting ophthalmic lenses and plano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions such as paints, and verification marks on security documents, e.g., documents such as banknotes, passports and drivers' licenses for which authentication or verification of authenticity may be desired. The six membered heterocyclic-fused naphthopyrans represented by graphic formula I exhibit color changes from colorless to colors ranging from red to violet.

Examples of contemplated naphthopyran compounds within the scope of the invention include the following:

a) 7,7-diphenyl-4-oxo-4H-7H-[1,3]dioxino[5',4':3,4]naphtho[1,2-b]pyran;

b) 7,7-di(4-methoxyphenyl)-4-oxo-4H-7H-[1,3]dioxino[5',4':3,4]naphtho[1,2-b]pyran;

c) 7-(4-methoxyphenyl)-7-phenyl-2-pentyl-4-oxo-4H-7H-[1,3]dioxino[5',4':3,4]naphtho[1,2-b]pyran;

d) 7,7-diphenyl-2-ethyl-4-oxo-4H-7H-[1,3]dioxino[5',4':3,4]naphtho[1,2-b]pyran;

e) 7,7-diphenyl-2-pentyl-4-oxo-4H-7H-[1,3]dioxino[5',4':3,4]naphtho[1,2-b]pyran;

f) 7,7-diphenyl-2-(2-methylpropyl)-4-oxo-4H-7H-[1,3]dioxino[5',4':3,4]naphtho[1,2-b]pyran;

g) 2,7,7-triphenyl-4-oxo-4H-7H-[1,3]dioxino[5',4':3,4]naphtho[1,2-b]pyran;

h) 7,7-diphenyl-2-(1-phenylethyl)-4-oxo-4H-7H-[1,3]dioxino[5',4':3,4]naphtho[1,2-b]pyran;

i) 3-methyl-7,7-diphenyl-2,4-dioxo-2,3,4,7-tetrahydro[1,3]oxazino[5',6':3,4]naphtho[1,2-b]pyran;

j) 3-(2-ethoxycarbonylethyl)-7,7-diphenyl-2,4 dioxo- 2,3,4,7-tetrahydro[1,3]oxazino[5',6':3,4]naphtho[1,2-b]pyran;

k) 3-hexyl-7,7-diphenyl-2,4-dioxo-2,3,4,7-tetrahydro[1,3]oxazino[5',6':3,4]naphtho[1,2-b]pyran;

l) 3-(2-methacryloyloxyethyl)-7,7-diphenyl-2,4-dioxo-2,3,4,7-tetrahydro[1,3]oxazino[5',6':3,4]naphtho[1,2-b]pyran;

m) 2,2,7,7-tetraphenyl-4-oxo-2,3,4,7-tetrahydro-1H-pyrimidino[5',4':3,4]naphtho[1,2-b]pyran;

n) 2,2,7,7-tetraphenyl-4-oxo-2,3,4,7-tetrahydro-1H-[1,3]oxazino[5',4':3,4]naphtho[1,2-b]pyran; and o) 7,7-diphenyl-1,2,4,7-tetrahydro-2,2-dimethylpyrano[3',4':3,4]naphtho[1,2-b]pyran.

It is contemplated that the organic photochromic naphthopyrans of the present invention may be used alone, in combination with other naphthopyrans of the present invention, or in combination with one or more other appropriate complementary organic photochromic materials, i.e., organic photochromic compounds having at least one activated absorption maxima within the range of between about 400 and 700 nanometers, or substances containing same, and may be incorporated, e.g., dissolved or dispersed, in a polymeric organic host material used to prepare photochromic articles and which color when activated to an appropriate hue.

Other than where otherwise indicated, all numbers expressing wavelengths, quantities of ingredients or reaction conditions used herein are to be understood as modified in all instances by the term "about".

Examples of complementary organic photochromic compounds include other naphthopyrans, chromenes and oxazines, substituted 2H-phenanthro[4,3-b]pyran and 3H-phenanthro[1,2-b]pyran compounds, benzopyran compounds having substituents at the 2-position of the pyran ring including a dibenzo-fused 5 member heterocyclic compound and a substituted or unsubstituted heterocyclic ring, such as a benzothieno or benzofurano ring fused to the benzene portion of the benzopyrans, spiro(benzindoline) naphthopyrans, spiro(indoline)benzopyrans, spiro(indoline) naphthopyrans, spiro(indoline)quinopyrans, spiro(indoline) pyrans, spiro(indoline)naphthoxazines, spiro(indoline) pyridobenzoxazines, spiro(benzindoline) pyridobenzoxazines, spiro(benzindoline)naphthoxazines, spiro(indoline)benzoxazines, and mixtures of such photochromic compounds. Many of such photochromic compounds are described in the open literature, e.g., U.S. Pat. Nos. 3,562,172; 3,567,605; 3,578,602; 4,215,010; 4,342,668; 4,816,584; 4,818,096; 4,826,977; 4,880,667; 4,931,219; 5,066,818; 5,238,931; 5,274,132; 5,384,077; 5,405,958; 5,429,774; 5,458,814; 5,466,398; 5,514,817; 5,552,090; 5,552,091; 5,565,147; 5,573,712; 5,578,252; 5,637,262; 5,645,767; 5,656,206; 5,658,500; 5,658,501; 5,674,432 and 5,698,141. Spiro(indoline)pyrans are also described in the text, *Techniques in Chemistry*, Volume III, "Photochromism", Chapter 3, Glenn H. Brown, Editor, John Wiley and Sons, Inc., New York, 1971.

Other complementary photochromic substances contemplated are photochromic metal-dithizonates, e.g. mercury dithizonates which are described in, for example, U.S. Pat. No. 3,361,706, fulgides and fulgimides, e.g. the 3-furyl and 3-thienyl fulgides and fulgimides which are described in U.S. Pat. No. 4,931,220 at column 20, line 5 through column 21, line 38.

The disclosures relating to such photochromic compounds in the aforedescribed patents are incorporated herein, in toto, by reference. The photochromic articles of the present invention may contain one photochromic compound or a mixture of photochromic compounds, as desired.

Each of the photochromic substances described herein may be used in amounts (or in a ratio) such that an organic host material to which the photochromic compounds or mixture of compounds is applied or in which they are incorporated exhibits a desired resultant color, e.g., a substantially neutral color when activated with unfiltered sunlight, i.e., as near a neutral color as possible given the colors of the activated photochromic compounds. Neutral gray and neutral brown colors are preferred.

A neutral gray color exhibits a spectrum that has relatively equal absorption in the visible range between 400 and 700 nanometers. A neutral brown color exhibits a spectrum in which the absorption in the 400–550 nanometer range is moderately larger than in the 550–700 nanometer range. An alternative way of describing color is in terms of its chromaticity coordinates, which describe the qualities of a color in addition to its luminance factor, i.e., its chromaticity. In the CIE system, the chromaticity coordinates are obtained by taking the ratios of the tristimulus values to their sum, e.g., $x=X/(X+Y+Z)$ and $y=Y/(X+Y+Z)$. Color as described in the CIE system can be plotted on a chromaticity diagram, usually a plot of the chromaticity coordinates x and y. See pages 47–52 of *Principles of Color Technology*, by F. W. Billmeyer, Jr., and Max Saltzman, Second Edition, John Wiley and Sons, N.Y. (1981). As used herein, a near neutral color is one in which the chromaticity coordinate values of "x" and "y" for the color are within the following ranges (D65 illuminant): x=0.260 to 0.400, y=0.280 to 0.400 following activation to 40 percent luminous transmission by exposure to solar radiation (Air Mass 1 or 2).

The amount of photochromic substance or composition containing same applied to or incorporated into a host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic substances. Typically, the more photochromic substance applied or incorporated, the greater is the color intensity up to a certain limit.

The relative amounts of the aforesaid photochromic compounds used will vary and depend in part upon the relative intensities of the color of the activated species of such compounds, and the ultimate color desired. Generally, the amount of total photochromic substance incorporated into or applied to a photochromic optical host material may range from 0.05 to 1.0, e.g., from 0.1 to 0.45, milligrams per square centimeter of surface to which the photochromic substance(s) is incorporated or applied.

The photochromic substances of the present invention may be applied to or incorporated into a host material such as a polymeric organic host material by various methods described in the art. Such methods include dissolving or dispersing the photochromic substance within the host material, e.g., casting it in place by adding the photochromic substance to the monomeric host material prior to polymerization; imbibition of the photochromic substance into the host material by immersion of the host material in a hot solution of the photochromic substance or by thermal transfer; providing the photochromic substance as a separate layer between adjacent layers of the host material, e.g., as a part of a polymeric film; applying the photochromic substance as part of a coating or film placed on the surface of the host material; and applying a photochromic polymeric overlay section to the surface of the host material. The overlay section may have a vision correcting feature. The term "imbibition" or "imbibe" is intended to mean and include permeation of the photochromic substance alone into the host material, solvent assisted transfer of the photochromic substance into a porous polymer, vapor phase transfer, and other such transfer mechanisms.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substances is in an unactivated state.

The host material will usually be transparent, but may be translucent or even opaque. The host material need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Preferably, the host color should not be such that it masks the color of the activated form of the photochromic substance, i.e., so the change in color is readily apparent to the observer. More preferably, the host material article is a solid transparent or optically clear material, e.g., materials suitable for optical applications, such as plano and ophthalmic lenses, windows, automotive transparencies, e.g., windshields, aircraft transparencies, plastic sheeting, polymeric films, etc.

The photochromic compounds of the present invention may be present in an organic solvent or an organic polymeric host. The organic solvent may be selected from the group consisting of benzene, toluene, methyl ethyl ketone, acetone, ethanol, tetrahydrofurfuryl alcohol, N-methyl pyrrolidinone, 2-methoxyethyl ether, xylene, cyclohexane, 3-methyl cyclohexanone, ethyl acetate, tetrahydrofuran, methanol, methyl propinate, ethylene glycol and mixtures thereof. Preferably, the organic solvent is selected from the group consisting of acetone, ethanol, tetrahydrofurfuryl alcohol, 2-methoxyethyl ether, 3-methyl cyclohexanone, N-methyl pyrrolidinone and mixtures thereof.

Preferably, the organic polymeric host material is a solid transparent or optically clear material, e.g., materials suitable for optical applications, such as plano and ophthalmic lenses, windows, automotive transparencies, e.g., windshields, aircraft transparencies, plastic sheeting, polymeric films, etc.

Examples of polymeric organic host materials are polymers prepared from individual monomers or mixtures of monomers selected from the following groups:

(a) diacrylate or dimethacrylate compounds represented by graphic formula XVIII:

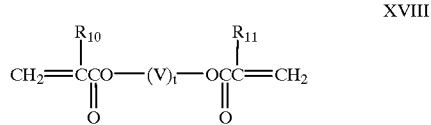

XVIII wherein $R_{10}$ and $R_{11}$ may be the same or different and are hydrogen or methyl, V is ($CH_2$), and t is an integer of from 1 to 20;

(b) diacrylate or dimethacrylate compounds represented by graphic formula XIX:

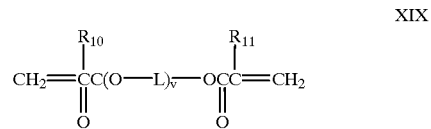

XIX wherein L is a straight or branched chain alkylene containing from 2 to 4 carbon atoms, and v is an integer of from 1 to 50; and (c) an acrylate or a methacrylate compound having an epoxy group represented by graphic formula XX:

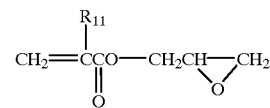

XX

In graphic formulae XVIII, XIX and XX, like letters used with respect to the definitions of different substituents have the same meaning.

Examples of diacrylate or dimethacrylate compounds, i.e., di(meth)acrylates, represented by graphic formula XVIII include butanediol di(meth)acrylate, hexanediol di(meth)acrylate and nonanediol di(meth)acrylate, and represented by graphic formula XIX include diethylene glycol dimethacrylate, triethylene glycol dimethacrylate and poly (oxyalkylene dimethacrylates), e.g., polyethylene glycol (600) dimethacrylate. Examples of acrylate or methacrylate compounds represented by graphic formula XX include glycidyl acrylate and glycidyl methacrylate.

Further examples of polymeric organic host materials which may be used with the photochromic compounds described herein include: polymers, i.e., homopolymers and copolymers, of the monomers and mixtures of monomers represented by graphic formulae XVIII, XIX and XX, bis(allyl carbonate) monomers, diisopropenyl benzene monomers, ethoxylated bisphenol A dimethacrylate monomers, ethylene glycol bismethacrylate monomers, poly (ethylene glycol) bismethacrylate monomers, ethoxylated phenol bismethacrylate monomers, alkoxylated polyhydric alcohol polyacrylate monomers, such as ethoxylated trimethylol propane triacrylate monomers, urethane acrylate monomers, such as those described in U.S. Pat. No. 5,373,033, and vinylbenzene monomers, such as those described in U.S. Pat. No. 5,475,074 and styrene; polymers, i.e., homopolymers and copolymers, of polyfunctional, e.g., mono-, di- or multi-functional, acrylate and/or methacrylate monomers, poly($C_1$–$C_{12}$ alkyl methacrylates), such as poly (methyl methacrylate), poly(alkoxylated phenol methacrylates), cellulose acetate, cellulose triacetate, cellulose acetate propionate, cellulose acetate butyrate, poly (vinyl acetate), poly(vinyl alcohol), poly(vinyl chloride), poly(vinylidene chloride), polyurethanes, polythiourethanes, thermoplastic polycarbonates, polyesters, poly(ethylene terephthalate), polystyrene, poly (alpha methylstyrene), copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers, e.g., ethyl acrylate, butyl acrylate.

Transparent copolymers and blends of transparent polymers are also suitable as host materials. Preferably, the host material is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis (allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483; poly(vinyl acetate), polyvinylbutyral, polyurethane, polythiourethane and polymers of members of the group consisting of diethylene glycol dimethacrylate monomers, diisopropenyl benzene monomers, ethoxylated bisphenol A dimethacrylate monomers, ethylene glycol bis-methacrylate monomers, poly(ethylene glycol) bismethacrylate monomers, ethoxylated phenol bismethacrylate monomers and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile.

More particularly, contemplated is use of the photochromic naphthopyrans of the present invention with optical organic resin monomers used to produce optically clear polymerizates, i.e., materials suitable for optical applications, such as for example plano and ophthalmic lenses, windows, and automotive transparencies. Such optically clear polymerizates may have a refractive index that may range from about 1.48 to about 1.75, e.g., from about 1.495 to about 1.66. Specifically contemplated are optical resins sold by PPG Industries, Inc. under the CR- designation, e.g., CR-307 and CR-407.

The present invention is more particularly described in the following examples which are intended as illustrative only, since numerous modifications and variations therein will be apparent to those skilled in the art.

EXAMPLE 1

Step 1

Phenyl-1,4-dihydroxy-2-naphthoate (5 grams) and 1,1-diphenyl-2-propyn-1-ol (4 grams) were added to a reaction flask containing 100 milliliters (mL) chloroform and stirred at room temperature. p-Toluene sulfonic acid (0.1 gram) was added to the reaction mixture and stirred for 10 hours. The solvent was evaporated leaving a residue which crystallized in diethyl ether. The crystals were separated via filtration, washed with hexane and oven dried yielding 6 grams of a product having a melting point of 158–160° C. A nuclear magnetic resonance (NMR) spectrum showed the product to have a structure consistent with 2,2-diphenyl-5-phenoxycarbonyl-6-hydroxy-2H-naphtho[1,2-b]pyran.

Step 2

One gram of the naphthopyran produced in Step 1 and triethylamine (0.5 gram) were added to a reaction flask containing chloroform (50 mL) and mixed. Paraformaldehyde (2.5 grams) was added to the reaction mixture and stirred for five hours. The mixture was filtered and the solvent in the filtrate was evaporated leaving an oily residue. The residue was dissolved in diethyl ether and washed with a five percent solution of hydrochloric acid and rewashed with water. The resulting organic layer was separated, dried and concentrated. The concentrate was crystallized from 1:1 ether:hexane mixture. The crystals were filtered, washed and oven dried yielding 0.6 gram of a product having a melting point of 234–236° C. An NMR spectrum showed the product to have a structure consistent with 7,7-diphenyl-4-oxo-4H-7H-[1,3]dioxino[5'4':3,4]naphtho[1,2-b]pyran.

EXAMPLE 2

The process of Example 1 was followed except that in Step 1, 1,1-bis(4-methoxyphenyl)-2-propyn-1-ol was used instead of 1,1-diphenyl-2-propyn-1-ol and in Step 2, two grams of the naphthopyran produced in Step 1 was used (instead of one gram thereof) and 4 grams of paraformaldehyde (instead of 2.5 grams thereof) was added to the reaction flask. Following the same workup procedure, 1.5 grams of a product having a melting point of 147–149° C. was obtained. An NMR spectrum showed the product to have a structure consistent with 7,7-di(4-methoxyphenyl)-4-oxo-4H-7H-[1,3]dioxino[5',4':3,4]naphtho[1,2-b]pyran.

EXAMPLE 3

The process of Example 1 was followed except that in Step 1, 1-(4-methoxyphenyl)-1-phenyl-2-propyn-1-ol was used instead of 1,1-diphenyl-2-propyn-1-ol and in Step 2, eight grams of the naphthopyran produced in Step 1 was used (instead of one gram thereof) and 15 grams of hexanal (instead of 2.5 grams thereof) was added to the reaction flask. Following the same workup procedure, 5 grams of a product having a melting point of 126–127° C. was obtained. An NMR spectrum showed the product to have a structure consistent with 7-(4-methoxyphenyl)-7-phenyl-2-pentyl-4-oxo-4H-7H-[1,3]dioxino[5',4':3,4]naphtho[1,2-b]pyran.

EXAMPLE 4

Two grams of the naphthopyran produced in Step 1 of Example 1, propanal (20 mL) and triethylamine (2 mL) were added to a reaction flask and stirred for three hours. Chloroform (50 mL) was added to the flask to dissolve the mixture. The solution was washed with a five percent solution of hydrochloric acid. The resulting organic layer was separated, washed with water, dried and concentrated. The concentrate crystallized from diethyl ether. The crystals were filtered, washed and oven dried yielding 1.7 grams of a product having a melting point of 163–164° C. An NMR spectrum showed the product to have a structure consistent with 7,7-diphenyl-2-ethyl-4-oxo-4H-7H-[1,3]dioxino[5',4':3,4]naphtho[1,2-b]pyran.

EXAMPLE 5

The process of Example 4 was followed except that 10 grams of a naphthopyran produced according to Step 1 of Example 1 was used, hexanal (20 mL) was used instead of propanaldehyde and DABCO (10 grams) was used instead of triethylamine. The process yielded 9.0 grams of a product having a melting point of 156–158° C. An NMR spectrum showed the product to have a structure consistent with 7,7-diphenyl-2-pentyl-4-oxo-4H-7H-[1,3]dioxino[5',4':3,4]naphtho[1,2-b]pyran.

EXAMPLE 6

The process of Example 4 was followed except that isovaleraldehyde was used instead of propanal yielding 1.6 grams of a product having a melting point of 158–160° C. An NMR spectrum showed the product to have a structure consistent with 7,7-diphenyl-2-(2-methylpropyl)-4-oxo-4H-7H-[1,3]dioxino[5',4':3,4]naphtho[1,2-b]pyran.

EXAMPLE 7

The process of Example 4 was followed except that benzaldehyde was used instead of propanal yielding 1.2 grams of a product having a melting point of 191–193° C. An NMR spectrum showed the product to have a structure consistent with 2,7,7-triphenyl-4-oxo-4H-7H-[1,3]dioxino [5',4':3,4]naphtho[1,2-b]pyran.

EXAMPLE 8

The process of Example 4 was followed except that 2-phenylpropionaldehyde was used instead of propanal yielding 1.6 grams of a product having a melting point of 206–208° C. An NMR spectrum showed the product to have a structure consistent with 7,7-diphenyl-2-(1-phenylethyl)-4-oxo-4H-7H-[1,3]dioxino[5',4':3,4]naphtho[1,2-b]pyran.

EXAMPLE 9

2,2-Diphenyl-5-methoxycarbonyl-6-hydroxy-2H-naphtho[1,2-b]pyran (3 grams) and DABCO (3 grams) were added to a reaction flask containing anhydrous dimethylformamide (40 mL) and stirred at room temperature. Methyl isocyanate (3 mL) was added dropwise to the mixture and stirred for five hours. Water (100 mL) was added to the mixture and extracted with diethyl ether. The ether layer was separated, washed with a five percent solution of hydrochloric acid, dried and concentrated. The concentrate was purified using a silica column with chloroform as the eluant yielding 1 gram of the desired product having a melting point of 245–247° C. and 1.2 grams of a byproduct having a melting point of 213–215° C. An NMR spectrum showed the desired product to have a structure consistent with 3-methyl-7,7-diphenyl-2,4-dioxo-2,3,4,7-tetrahydro[1,3] oxazino[5',6':3,4]naphtho[1,2-b]pyran and the byproduct to have a structure consistent with 2,2-diphenyl-5-methoxycarbonyl-6-(N-methylamino)carbonyloxy-2H-naphtho[1,2-b]pyran.

EXAMPLE 10

The process of Example 9 was followed except that 5 grams of the naphthopyran were used and ethyl-1-isocyanopropionate (10 mL) was used instead of methyl isocyanate and triethylamine was used instead of DABCO. A single product was isolated and had a melting point of 187–188° C. An NMR spectrum showed the product to have a structure consistent with 3-(2-ethoxycarbonylethyl)-7,7-diphenyl-2,4-dioxo-2,3,4,7-tetrahydro[1,3]oxazino[5',6':3, 4]naphtho[1,2-b]pyran.

EXAMPLE 11

The process of Example 9 was followed except that 15 grams of the naphthopyran were used and n-hexyl isocyanate (20 mL) was used instead of methyl isocyanate and triethylamine was used instead of DABCO. A single product was isolated and had a melting point of 172–174° C. An NMR spectrum showed the product to have a structure consistent with 3-hexyl-7,7-diphenyl-2,4-dioxo-2,3,4,7-tetrahydro[1,3]oxazino[5',6':3,4]naphtho[1,2-b]pyran.

EXAMPLE 12

The process of Example 9 was followed except that 5 grams of the naphthopyran were used and 2-methacryloyloxy ethyl isocyanate (10 mL) was used instead of methyl isocyanate and triethylamine was used instead of DABCO. A single product was isolated and had a melting point of 198–200° C. An NMR spectrum showed the product to have a structure consistent with 3-(2-methacryloyloxyethyl)-7,7-diphenyl-2,4-dioxo-2,3,4,7-tetrahydro[1,3]oxazino[5',6':3,4]naphtho[1,2-b]pyran.

EXAMPLE 13

Benzophenone imine (10 grams) was added to a reaction flask containing tetrahydrofuran (THF) (100 mL). One equivalent of isopropyl magnesium bromide was slowly added to the mixture to produce a benzophenone imino magnesium bromide Grignard reagent. 2,2-Diphenyl-5-methoxycarbonyl-6-methoxy-2H-naphtho[1,2-b]pyran (3 grams) dissolved in 20 mL THF was added to the reagent mixture and stirred for two hours. A ten percent solution of hydrochloric acid (100 mL) was added and stirred for one half hour. The mixture was extracted with diethyl ether, washed, dried and concentrated. A solid product immediately formed in the concentrate. The solid product (Compound 13) was filtered, washed and dried and found to have a melting point of 274–276° C. The filtrate was passed through a silica column yielding a second desired product (Compound 13A) and a byproduct. NMR spectra and mass spectra showed Compound 13 (major product) to have a structure consistent with 2,2,7,7-tetraphenyl-4-oxo-2,3,4,7-tetrahydro-1H-pyrimidino[5',4':3,4]naphtho[1,2-b]pyran, Compound 13A (minor product) to have a structure consistent with 2,2,7,7-tetraphenyl-4-oxo-2,3,4,7-tetrahydro-1H-[1,3]oxazino[5',4':3,4]naphtho[1,2-b]pyran and the byproduct to have a structure consistent with 2,2-diphenyl-5-carbamoyl-6-methoxy-2H-naphtho[1,2-b]pyran.

EXAMPLE 14

Step 1

2,2-Diphenyl-5-methoxycarbonyl-6-methoxy-2H-naphtho[1,2-b]pyran (2 grams) dissolved in THF (10 mL) was slowly added to a reaction flask containing freshly prepared 2-methylpropylene-1-magnesium bromide, a 20% excess, and stirred for three hours. A 100 mL mixture of ice and a five percent solution of hydrochloric acid was added to the mixture and stirred for one half hour. The organic layer was separated, washed, dried and concentrated. The concentrate was purified by column chromatography using a 1:1 chloroform:hexane mixture as the eluant. The fractions with the desired product were collected and combined. The solvent was evaporated leaving 1.2 grams of an oily residue. An NMR spectrum showed the product to have a structure consistent with 2,2-diphenyl-5-methoxycarbonyl-6-(2-methylprop-1-enyl)-2H-naphtho[1,2-b]pyran.

Step 2

One gram of the naphthopyran produced in Step 1, trimethyl silyl chloride (1 gram) and sodium iodide (1 gram) were added to a reaction flask containing anhydrous acetonitrile (30 mL) and stirred at 50° C. for eight hours. Water (50 mL) was added to the mixture, and the mixture was extracted with diethyl ether. The ether layer was washed with 5% sodium thiosulfate solution followed by water. The washed ether layer was dried, concentrated and passed through a silica gel column. The fractions containing the desired product were collected and concentrated yielding 100 mg of an oily product. An NMR spectrum showed the product to have a structure consistent with 7,7-diphenyl-1, 2,4,7-tetrahydro-2,2-dimethylpyrano[3',4':3,4]naphtho[1,2-b]pyran.

EXAMPLE 15

Part A

Testing was done with the photochromic compounds prepared in Examples 1–14 in the following manner. A quantity of each photochromic compound, except Compounds 13A and 14, calculated to yield a $1.5 \times 10^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). Each photochromic compound was dissolved into the monomer blend by stirring and gentle heating. After a clear solution was obtained, it was poured into a flat sheet mold having the interior dimensions of 2.2 mm×6 inches (15.24 cm)×6 inches (15.24 cm). The mold was sealed and placed in a horizontal air flow, programmable oven programmed to increase the temperature from 40° C. to 95° C. over a 5 hour interval, hold the temperature at 95° C. for 3 hours, lower it to 60° C. over a 2 hour interval and then hold at 60° C. for 16 hours. After the mold was opened, the polymer sheet was cut using a diamond blade saw into 2 inch (5.1 centimeters) test squares.

The compound of Example 13 identified as 13A and the compound of Example 14 were dissolved in diethylene glycol dimethyl ether. The concentration of the resulting solution was approximately 0.5 milligram per milliliter. Each solution was tested in a UV/Visible Spectrophotometer to determine the lambda max (Vis).

Part B

The photochromic test squares prepared in Part A were tested for photochromic response on an optical bench. Prior to testing on the optical bench, the photochromic test squares were exposed to 365 nanometer ultraviolet light for about 15 minutes to activate the photochromic compounds and then placed in a 76° C. oven for about 15 minutes to bleach or inactivate the photochromic compounds. The test squares were then cooled to room temperature, exposed to fluorescent room lighting for at least 2 hours and then kept covered for at least 2 hours prior to testing on an optical bench maintained at 72° F. (22.2° C.). The bench was fitted with a 150 watt Xenon arc lamp, a remote controlled shutter, a copper sulfate bath acting as a heat sink for the arc lamp, a Schott WG-320 nm cut-off filter which removes short wavelength radiation; neutral density filter(s) and a sample holder in which the square to be tested was inserted. The power output of the optical bench, i.e., the dosage of light that the sample lens would be exposed to, was calibrated with a photochromic test square used as a reference standard. This resulted in a power output ranging from 0.15 to 0.20 milliwatts per square centimeter (mW/cm$^2$). Measurement of the power output was made using a GRASEBY Optronics Model S-371 portable photometer (Serial #21536) with a UV-A detector (Serial #22411) or comparable equipment. The UV-A detector was placed into the sample holder and the light output was measured. Adjustments to the power output were made by increasing or decreasing the lamp wattage or by adding or removing neutral density filters in the light path.

A monitoring, collimated beam of light from a tungsten lamp was passed through the square at a small angle (approximately 30°) normal to the square. After passing through the square, the light from the tungsten lamp was directed to a detector through Spectral Energy Corp. GM-200 monochromator set at the previously determined visible lambda max of the photochromic compound being measured. The output signals from the detector were processed by a radiometer.

Change in optical density ($\Delta OD$) was determined by inserting a test square in the bleached state into the sample holder, adjusting the transmittance scale to 100%, opening the shutter from the Xenon lamp to provide ultraviolet radiation to change the test square from the bleached state to an activated (i.e., darkened) state, measuring the transmittance in the activated state, and calculating the change in optical density according to the formula: $\Delta OD = \log(100/\% Ta)$, where % Ta is the percent transmittance in the activated state and the logarithm is to the base 10.

The optical properties of the photochromic compound in the test squares are reported in Table 1. The $\Delta OD/\min$, which represents the sensitivity of the photochromic compound's response to UV light, was measured over the first five (5) seconds of UV exposure, then expressed on a per minute basis. The saturation optical density ($\Delta OD@$ Saturation) was taken under identical conditions as the $\Delta OD/\min$, except UV exposure was continued for 15 minutes. The lambda max (Vis) is the wavelength in nanometers (nm) in the visible spectrum at which the maximum absorption of the activated (colored) form of the photochromic compound in a test square occurs. The lambda max (Vis) wavelength was determined by testing the photochromic test square polymerizates of Part A in a Varian Cary 3 UV-Visible spectrophotometer. The Bleach Rate (T 1/2) is the time interval in seconds for the absorbance of the activated form of the photochromic compound in the test squares to reach one half the highest absorbance at room temperature (72° F., 22.2° C.) after removal of the source of activating light.

TABLE 1

| Compound Example | lambda max (Vis) nanometers | Sensitivity $\Delta OD/\min$ | $\Delta OD @$ Saturation | Bleach Rate T 1/2 (sec) |
|---|---|---|---|---|
| 1 | 472 | 0.76 | 1.89 | 220 |
| 2 | 510 | 0.74 | 0.67 | 51 |
| 3 | 496 | 0.75 | 1.28 | 117 |
| 4 | 474 | 0.67 | 1.71 | 248 |
| 5 | 478 | 0.67 | 1.74 | 254 |
| 6 | 475 | 0.64 | 1.72 | 240 |
| 7 | 476 | 0.60 | 1.46 | 248 |
| 8 | 475 | 0.63 | 1.58 | 251 |
| 9 | 469 | 0.41 | 0.40 | 51 |
| 10 | 468 | 0.44 | 0.38 | 42 |
| 11 | 471 | 0.46 | 0.41 | 53 |
| 12 | 467 | 0.26 | 0.32 | 140 |
| 13 | 512 | 0.62 | 2.45 | 533 |
| 13A | 471 | — | — | — |
| 14 | 460 | — | — | — |

The results of Table 1 show that test squares prepared using the Compounds of Examples 1 through 14 and the solutions of Compounds 13A and Example 14 demonstrate a range of colors from wavelengths of 460 nm to 512 nm, coloration rates (sensitivity) from 0.26 to 0.76, activated intensity ($\Delta OD$ at Saturation) from 0.40 to 2.45, and fade or bleach from 42 to 533 seconds.

The present invention has been described with reference to specific details of particular embodiments thereof. It is not intended that such details be regarded as limitation upon the scope of the invention except insofar as to the extent that they are included in the accompanying

We claim:
1. A naphthopyran compound represented by the following graphic formula:

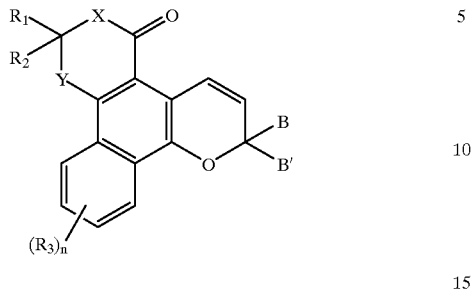

wherein,
(a) $R_1$ and $R_2$ together form an oxo group or $R_1$ is hydrogen and $R_2$ is hydrogen, $C_1$–$C_6$ alkyl, $C_3$–$C_7$ cycloalkyl, allyl, phenyl, mono- or di-substituted phenyl, benzyl, mono-substituted benzyl, naphthyl, mono- or di-substituted naphthyl, $C_4$–$C_{12}$ bicycloalkyl, linear or branched $C_3$–$C_{12}$ alkenyl, $C_1$–$C_6$ alkoxy carbonyl($C_1$–$C_6$)alkyl, methacryloxy($C_1$–$C_6$)alkyl, acryloxy($C_1$–$C_6$)alkyl, $C_1$–$C_4$ acyloxy($C_1$–$C_6$)alkyl, $C_1$–$C_6$ alkoxy($C_1$–$C_6$)alkyl or the unsubstituted, mono- or di-substituted heteroaromatic groups pyridyl, furanyl, benzofuran-2-yl, benzyfuran-3-yl, thienyl, benzothien-2-yl, benzothien-3-yl, dibenzofuranyl, dibenzothienyl, carbazolyl, benzopyridyl and indolyl, each of said phenyl, benzyl, naphthyl and heteroaromatic group substituents being $C_1$–$C_6$ alkyl, $C_1$–$C_6$ alkoxy, morpholino, di($C_1$–$C_6$)alkylamino, chloro or fluoro;
(b) $R_3$ is selected from the group consisting of $C_1$–$C_6$ alkyl, $C_1$–$C_6$ alkoxy, chloro, fluoro, phenyl, mono- and di-substituted phenyl, benzyl or mono-substituted benzyl, $C_3$–$C_7$ cycloalkyl, aryloxy, di($C_1$–$C_6$) alkylamino, morpholino, thiomorpholino, piperidino, pyridyl, tetrahydroquinolino, isoquinolino, aziridino, diarylamino, N—($C_1$–$C_6$)alkyl piperizino and N-aryl piperizino, wherein the aryl groups are phenyl or naphthyl, each of said phenyl and benzyl substituents being $C_1$–$C_6$ alkyl, $C_1$–$C_6$ alkoxy, fluoro and chloro, and n is the integer 0, 1 or 2;
(c) X is oxygen or —N($R_4$)—, wherein $R_4$ is hydrogen $C_1$–$C_6$ alkyl, $C_3$–$C_7$ cycloalkyl, allyl, vinyl, $C_1$–$C_5$ acyl, phenyl, mono- and di-substituted phenyl, benzyl, mono-substituted benzyl, $C_1$–$C_4$ alkoxycarbonyl ($C_1$–$C_6$)alkyl, methacryloxy($C_1$–$C_6$)alkyl, acryloyloxy ($C_1$–$C_6$)alkyl, phenyl($C_1$–$C_6$)alkyl, naphthyl, $C_4$–$C_{12}$ bicycloalkyl, $C_2$–$C_4$ acyloxy or the unsubstituted or substituted heteroaromatic groups pyridyl, furanyl, benzofuran-2-yl, benzofuran-3-yl, thienyl, benzothien-2-yl, benzothien-3-yl, dibenzofuranyl, dibenzothienyl, carbazolyl, benzopyridyl and indolyl, each of said phenyl, benzyl and heteroaromatic group substituents being $C_1$–$C_6$ alkyl or $C_1$–$C_6$ alkoxy;
(d) Y is oxygen, —N($R_4$)— or —C($R_5$)$R_6$—, wherein $R_5$ and $R_6$ are each hydrogen, $C_1$–$C_6$ alkyl or $C_3$–$C_7$ cycloalkyl, with the proviso that when Y is —(C($R_5$)$R_6$)—, X is oxygen; and
(e) B and B' are each selected from the group consisting of:
(i) the unsubstituted, mono-, di- and tri-substituted aryl groups, phenyl and naphthyl;
(ii) the unsubstituted, mono- and di-substituted heteroaromatic groups pyridyl, furanyl, benzofuran-2-yl, benzofuran-3-yl, thienyl, benzothien-2-yl, benzothien-3-yl, dibenzofuranyl, dibenzothienyl, carbazolyl, benzopyridyl, indoloyl and fluorenyl, each of said aryl and heteroaromatic substituents in parts (i) and (ii) being selected from the group consisting of hydroxy, aryl, i.e., phenyl and naphthyl, mono($C_1$–$C_6$)alkoxyaryl, di($C_1$–$C_6$)alkoxyaryl, mono($C_1$–$C_6$)alkylaryl, di($C_1$–$C_6$)alkylaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy ($C_1$–$C_6$)alkoxy, aryl($C_1$–$C_6$)alkyl, aryl($C_1$–$C_6$)alkoxy, aryloxy, aryloxy($C_1$–$C_6$)alkyl, aryloxy ($C_1$–$C_6$)alkoxy, mono- and di-($C_1$–$C_6$)alkylaryl ($C_1$–$C_6$)alkyl, mono- and di-($C_1$–$C_6$)alkoxyaryl ($C_1$–$C_6$)alkyl, mono- and di-($C_1$–$C_6$)alkylaryl ($C_1$–$C_6$)alkoxy, mono- and di-($C_1$–$C_6$)alkoxyaryl ($C_1$–$C_6$)alkoxy, amino, mono($C_1$–$C_6$)alkylamino, di($C_1$–$C_6$)alkylamino, diarylamino, piperazino, N—($C_1$–$C_6$)alkylpiperazino, N-arylpiperazino, aziridino, indolino, piperidino, morpholino, thiomorpholino, tetrahydroquinolino, tetrahydroisoquinolino, pyrryl, $C_1$–$C_6$ alkyl, $C_1$–$C_6$ chloroalkyl, $C_1$–$C_6$ fluoroalkyl, $C_1$–$C_6$ alkoxy, mono ($C_1$–$C_6$)alkoxy($C_1$–$C_4$)alkyl, acryloxy, methacryloxy, bromo, chloro and fluoro;
(iii) the groups represented by the following graphic formulae:

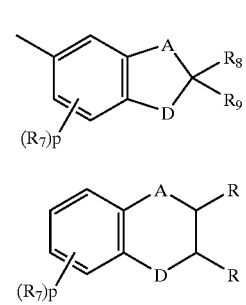

wherein A may be carbon or oxygen and D may be oxygen or substituted nitrogen, provided that when D is substituted nitrogen, A is carbon, said nitrogen substituents being selected from the group consisting of hydrogen, $C_1$–$C_6$ alkyl and $C_2$–$C_6$ acyl; each $R_7$ is $C_1$–$C_6$ alkyl, $C_1$–$C_6$ alkoxy, hydroxy, chloro or fluoro; $R_8$ and $R_9$ are each hydrogen or $C_1$–$C_6$ alkyl; and p is the integer 0, 1 or 2;
(iv) $C_1$–$C_6$ alkyl, $C_1$–$C_6$ chloroalkyl, $C_1$–$C_6$ fluoroalkyl, $C_1$–$C_6$ alkoxy($C_1$–$C_4$)alkyl, $C_3$–$C_6$ cycloalkyl, mono($C_1$–$C_6$)alkoxy($C_3$–$C_6$)cycloalkyl, mono($C_1$–$C_6$)alkyl($C_3$–$C_6$)cycloalkyl, chloro ($C_3$–$C_6$)cycloalkyl, fluoro($C_3$–$C_6$)cycloalkyl and $C_4$–$C_{12}$ bicycloalkyl; and
(v) the group represented by the following graphic formula:

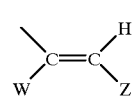

wherein W may be hydrogen or $C_1$–$C_4$ alkyl and Z may be selected from the unsubstituted, mono-, and di-substituted members of the group consisting of naphthyl, phenyl, furanyl and thienyl, each of said group substituents in this part (v) being $C_1$–$C_4$ alkyl, $C_1$–$C_4$ alkoxy, fluoro or chloro; or (vi) B and B' taken together form fluoren-9-ylidene, mono-, or di-substituted fluoren-9-ylidene or form a member selected from the group consisting of saturated $C_3$–$C_{12}$ spiro-monocyclic hydrocarbon rings, saturated $C_7$–$C_{12}$ spirobicylic hydrocarbon rings, and saturated $C_7$–$C_{12}$ spiro-tricyclic hydrocarbon rings, each of said fluoren-9-ylidene substituents being selected from the group consisting of $C_1$–$C_4$ alkyl, $C_1$–$C_4$ alkoxy, fluoro and chloro.

2. The naphthopyran of claim 1 wherein, (a) $R_1$ is hydrogen and $R_2$ is hydrogen, $C_1$–$C_5$ alkyl, $C_3$–$C_6$ cycloalkyl, phenyl, mono- or di-substituted phenyl, benzyl or mono-substituted benzyl, each of said phenyl and benzyl group substituents being $C_1$–$C_4$ alkyl or $C_1$–$C_4$ alkoxy;

(b) $R_3$ is selected from the group consisting of $C_1$–$C_4$ alkyl, $C_1$–$C_4$ alkoxy, fluoro, phenyl and aryloxy, and n is the integer 0, 1, or 2;

(c) X is oxygen or —N($R_4$)—, wherein $R_4$ is hydrogen, $C_1$–$C_3$ alkyl, methacryloxy($C_1$–$C_6$)alkyl or acryloxy ($C_1$–$C_6$)alkyl;

(d) Y is oxygen, —NH— or —$CH_2$—; and (e) B and B' are each selected from the group consisting of:

(i) phenyl, mono-substituted phenyl and di-substituted phenyl;

(ii) the unsubstituted, mono- and di-substituted heteroaromatic groups furanyl, benzofuran-2-yl, thienyl, benzothien-2-yl, dibenzofuranyl, aryloxy and diarylamino, each of said phenyl and heteroaromatic substituents being selected from the group consisting of di($C_1$–$C_3$)alkylamino, piperidino, morpholino, pyrryl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$)alkoxy($C_1$–$C_3$)alkyl, fluoro and chloro;

(iii) the groups represented by the graphic formulae IIA and IIB, wherein A is carbon and D is oxygen, $R_7$ is $C_1$–$C_3$ alkyl or $C_1$–$C_3$ alkoxy, $R_8$ and $R_9$ are each hydrogen or $C_1$–$C_4$ alkyl, and p is the integer 0 or 1;

(iv) $C_1$–$C_4$ alkyl; and (v) the group represented by the graphic formula IIC wherein W is hydrogen or methyl and Z is phenyl or mono-substituted phenyl, said phenyl substituent being selected from the group consisting of $C_1$–$C_3$ alkyl, $C_1$–$C_3$ alkoxy and fluoro; or (vi) B and B' taken together form fluoren-9-ylidene, mono-substituted fluoren-9-ylidene or a member selected from the group consisting of saturated $C_3$–$C_8$ spiro-monocyclic hydrocarbon rings, saturated $C_7$–$C_{10}$ spiro-bicyclic hydrocarbon rings, and saturated $C_7$–$C_{10}$ spiro-tricyclic hydrocarbon rings, said fluoren-9-ylidene substituent being selected from the group consisting of $C_1$–$C_3$ alkyl, $C_1$–$C_3$ alkoxy, fluoro and chloro.

3. The naphthopyran of claim 2 wherein, (a) $R_1$ is hydrogen and $R_2$ is hydrogen, $C_1$–$C_5$ alkyl or phenyl;

(b) $R_3$ is selected from the group consisting of $C_1$–$C_3$ alkyl, $C_1$–$C_3$ alkoxy, phenyl and aryloxy and n is the integer 0, 1, or 2;

(c) B and B' are each selected from the group consisting of:

(i) phenyl, mono- and di-substituted phenyl;

(ii) the unsubstituted, mono- and di-substituted heteroaromatic groups furanyl, benzofuran-2-yl, thienyl, benzothien-2-yl, dibenzofuranyl, aryloxy and diarylamino, each of said phenyl and heteroaromatic substituents being selected from the group consisting of $C_1$–$C_3$ alkyl, $C_1$–$C_3$ alkoxy and fluoro; and (iii) the group represented by graphic formula IIA, wherein A is carbon and D is oxygen, $R_7$ is $C_1$–$C_3$ alkyl or $C_1$–$C_3$ alkoxy, $R_8$ and $R_9$ are each hydrogen or $C_1$–$C_3$ alkyl, and p is the integer 0 or 1; or (iv) B and B' taken together form fluoren-9-ylidene, adamantylidene, bornylidene, norbornylidene, or bicyclo[3.3.1]nonan-9-ylidene.

4. A naphthopyran compound selected from the group consisting of:

a) 7,7-diphenyl-4-oxo-4H-7H-[1,3]dioxino[5',4':3,4]naphtho[1,2-b]pyran;

b) 7,7-di(4-methoxyphenyl)-4-oxo-4H-7H-[1,3]dioxino[5',4':3,4]naphtho[1,2-b]pyran;

c) 7-(4-methoxyphenyl)-7-phenyl-2-pentyl-4-oxo-4H-7H-[1,3]dioxino[5',4':3,4]naphtho[1,2-b]pyran;

d) 7,7-diphenyl-2-ethyl-4-oxo-4H-7H-[1,3]dioxino[5',4':3,4]naphtho[1,2-b]pyran;

e) 7,7-diphenyl-2-pentyl-4-oxo-4H-7H-[1,3]dioxino[5',4':3,4]naphtho[1,2-b]pyran;

f) 7,7-diphenyl-2-(2-methylpropyl)-4-oxo-4H-7H-[1,3]dioxino[5',4':3,4]naphtho[1,2-b]pyran;

g) 2,7,7-triphenyl-4-oxo-4H-7H-[1,3]dioxino[5',4':3,4]naphtho[1,2-b]pyran;

h) 7,7-diphenyl-2-(1-phenylethyl)-4-oxo-4H-7H-[1,3]dioxino[5',4':3,4]naphtho[1,2-b]pyran;

i) 3-methyl-7,7-diphenyl-2,4-dioxo-2,3,4,7-tetrahydro[1,3]oxazino[5',6':3,4]naphtho[1,2-b]pyran;

j) 3-(2-ethoxycarbonylethyl)-7,7-diphenyl-2,4-dioxo-2,3,4,7-tetrahydro[1,3]oxazino[5',6':3,4]naphtho[1,2-b]pyran;

k) 3-hexyl-7,7-diphenyl-2,4-dioxo-2,3,4,7-tetrahydro[1,3]oxazino[5',6':3,4]naphtho[1,2-b]pyran;

l) 3-(2-methacryloyloxyethyl)-7,7-diphenyl-2,4-dioxo-2,3,4,7-tetrahydro[1,3]oxazino[5',6':3,4]naphtho[1,2-b]pyran;

m) 2,2,7,7-tetraphenyl-4-oxo-2,3,4,7-tetrahydro-1H-pyrimidino[5',4':3,4]naphtho[1,2-b]pyran;

n) 2,2,7,7-tetraphenyl-4-oxo-2,3,4,7-tetrahydro-1H-[1,3]oxazino[5',4':3,4]naphtho[1,2-b]pyran; and o) 7,7-diphenyl-1,2,4,7-tetrahydro-2,2-dimethylpyrano[3',4':3,4]naphtho[1,2-b]pyran.

5. A photochromic article comprising a polymeric organic host material and a photochromic amount of the naphthopyran compound of claim 1.

6. The photochromic article of claim 5 wherein the polymeric organic host material is selected from the group consisting of poly($C_1$–$C_{12}$ alkyl methacrylates), poly(oxyalkylene dimethacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, polythiourethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of bis(allyl carbonate) monomers, polyfunctional acrylate monomers, polyfunctional methacrylate monomers, diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers, alkoxylated polyhydric alcohol acrylate monomers, styrene monomers, urethane acrylate monomers, glycidyl acrylate monomers, glycidyl methacrylate monomers and diallylidene pentaerythritol monomers.

7. The photochromic article of claim 6 wherein the polymeric organic host material is a solid transparent polymer selected from the group consisting of poly(methyl methacrylate), poly(ethylene glycol bismethacrylate), poly (ethoxylated bisphenol A dimethacrylate), thermoplastic polycarbonate, poly(vinyl acetate), polyvinylbutyral, polyurethane, polythiourethane and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers.

8. The photochromic article of claim 7 wherein the photochromic compound is present in an amount of from 0.05 to 1.0 milligram per square centimeter of organic host material surface to which the photochromic substance(s) is incorporated or applied.

9. The photochromic article of claim 8 wherein said transparent polymer is an optical element.

10. The photochromic article of claim 9 wherein said optical element is a lens.

11. A photochromic article comprising a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane, polythiourethane and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers, and a photochromic amount of the naphthopyran compound of claim 3.

12. A photochromic article comprising a polymerizate of an optical organic resin monomer and a photochromic amount of the naphthopyran compound of claim 1.

13. The photochromic article of claim 12 wherein the refractive index of the polymerizate is from about 1.48 to about 1.75.

14. The photochromic article of claim 13 wherein the refractive index of the polymerizate is from about 1.495 to about 1.66.

15. A photochromic article comprising, in combination, a solid transparent polymeric organic host material, and a photochromic amount of each of (a) at least one naphthopyran compound of claim 1, and (b) at least one other organic photochromic compound having at least one activated absorption maxima within the range of between about 400 and 700 nanometers.

16. The photochromic article of claim 15 wherein the polymeric organic host material is selected from the group consisting of poly($C_1$–$C_{12}$ alkyl methacrylates), poly (oxyalkylene dimethacrylates), poly(alkoxylated phenol methacrylates), cellulose acetate, cellulose triacetate, cellulose acetate propionate, cellulose acetate butyrate, poly (vinyl acetate), poly(vinyl alcohol), poly(vinyl chloride), poly(vinylidene chloride), thermoplastic polycarbonates, polyesters, polyurethanes, polythiourethanes, poly(ethylene terephthalate), polystyrene, poly(alpha methylstyrene), copoly(styrene-methylmethacrylate) copoly(styrene-acrylonitrile), polyvinylbutyral and polymers of members of the group consisting of bis(allyl carbonate) monomers, polyfunctional acrylate monomers, polyfunctional methacrylate monomers, diethylene glycol dimethacrylate monomers, ethoxylated bisphenol A dimethacrylate monomers, diisopropenyl benzene monomers, ethylene glycol bismethacrylate monomers, poly(ethylene glycol) bismethacrylate monomers, ethoxylated phenol bismethacrylate monomers, alkoxylated polyhydric alcohol acrylate monomers, styrene monomers, urethane acrylate monomers, glycidyl acrylate monomers, glycidyl methacrylate monomers and diallylidene pentaerythritol monomers.

17. The photochromic article of claim 16 wherein the polymeric organic host material is a solid transparent homopolymer or copolymer selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane, polythiourethane and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers.

18. The photochromic article of claim 15 wherein the organic photochromic compound (b) is selected from the group consisting of other naphthopyrans, chromenes, oxazines, metal-dithizonates, fulgides and fulgimides.

19. The photochromic article of claim 18 wherein the total amount of photochromic compound present is from 0.05 to 1.0 milligram per square centimeter of organic host material surface to which the photochromic substance(s) is incorporated or applied.

20. The photochromic article of claim 18 wherein said transparent polymeric organic host material is an optical element.

21. The photochromic article of claim 20 wherein said optical element is a lens.

22. A photochromic article comprising, in combination, a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane, polythiourethane and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers, and a photochromic amount of each of (a) at least one naphthopyran compound of claim 3, and (b) at least one other organic photochromic compound having at least one activated absorption maxima within the range of between about 400 and 700 nanometers.

* * * * *